US009271660B2

(12) United States Patent
Luo et al.

(10) Patent No.: US 9,271,660 B2
(45) Date of Patent: Mar. 1, 2016

(54) VIRTUAL PROSTHETIC LIMB SYSTEM

(76) Inventors: Gangming Luo, Elmhurst, NY (US);
Jonathan J. Kaufman, Brooklyn, NY (US)

( * ) Notice: Subject to any disclaimer, the term of this patent is extended or adjusted under 35 U.S.C. 154(b) by 1150 days.

(21) Appl. No.: 13/175,113

(22) Filed: Jul. 1, 2011

(65) Prior Publication Data

US 2012/0004579 A1     Jan. 5, 2012

Related U.S. Application Data

(60) Provisional application No. 61/398,794, filed on Jul. 2, 2010.

(51) Int. Cl.
| | |
|---|---|
| *A61B 5/103* | (2006.01) |
| *A61B 5/0488* | (2006.01) |
| *A61F 2/68* | (2006.01) |
| *A61F 4/00* | (2006.01) |
| *G06F 19/00* | (2011.01) |
| *A61B 5/11* | (2006.01) |
| *A61F 2/72* | (2006.01) |
| *A61F 2/70* | (2006.01) |
| *A61F 2/76* | (2006.01) |

(52) U.S. Cl.
CPC .............. *A61B 5/04888* (2013.01); *A61F 2/68* (2013.01); *A61F 4/00* (2013.01); *G06F 19/3437* (2013.01); *A61B 5/1127* (2013.01); *A61F 2/72* (2013.01); *A61F 2002/6827* (2013.01); *A61F 2002/705* (2013.01); *A61F 2002/707* (2013.01); *A61F 2002/764* (2013.01)

(58) Field of Classification Search
CPC ...... A61B 5/0488; A61B 5/1127; A61F 2/68; A61F 4/00; G06F 19/3437
USPC ................... 600/595, 454; 607/45, 54; 606/80
See application file for complete search history.

(56) References Cited

U.S. PATENT DOCUMENTS

| 6,421,048 B1 * | 7/2002 | Shih et al. ..................... 345/419 |
| 2008/0009771 A1 * | 1/2008 | Perry et al. .................... 600/587 |

OTHER PUBLICATIONS

Besier Thor F. et al., "Repeatability of Gait Data Using a Functional Hip Joint Centre and a Mean Helical Knee Axis," 36 Journal of Biomechanics pp. 1159-68 (2003).
Burck, James et al. "Developing the World's Most Advanced Prosthetic Arm Using Model-Based Design," TheMathWorks News &Notes (2009).
Orsborn, Amy et al. "Simulation of an Above-Elbow Myoelectric Prosthetic Arm for Development of an Implanted Myoelectric Control System," SOURCE Annual Symposium for Undergraduate Research, Case Western Reserve University (Apr. 2007).
Schwartz, Andrew B. et al. "Extraction Algorithms for Cortical Control of Arm Prosthetics," 11 Current Opinion in Neurobiology pp. 701-707 (2001).

(Continued)

*Primary Examiner* — Max Hindenburg
*Assistant Examiner* — Jonathan M Foreman
(74) *Attorney, Agent, or Firm* — Reising Ethington P.C.

(57) ABSTRACT

A system for configuring a prosthetic limb for use by a living being is provided. The system includes an electronic control unit (ECU) configured to receive a control signal generated in response to a command from the living being and to generate a plurality of virtual bodies on a display including members of a virtual prosthetic limb and at least one virtual object. The ECU is further configured to control movement of at least one member of the virtual limb responsive to the control signal, to determine a contact force between first and second virtual bodies of the plurality of virtual bodies upon engagement between the first and second bodies caused by movement of one of the one member of the virtual limb and the at least one virtual object and to adjust a position of at least one of the first and second bodies responsive to the contact force.

20 Claims, 2 Drawing Sheets

(56) References Cited

OTHER PUBLICATIONS

Taylor, Dawn M. et al. "Using Virtual Reality to Test the Feasibility of Controlling an Upper Limb FES System Directly from Multiunit Activity in the Motor Cortex," Proceedings of the 6th Annual IFESS Conference (2001).

Velliste, Meel et al. "Cortical Control of a Prosthetic Arm for Self-Feeding," 453 Nature pp. 1098-1101 (2008).

* cited by examiner

VIRTUAL PROSTHETIC LIMB SYSTEM

This application claims priority to U.S. Provisional Patent Application No. 61/398,794 filed Jul. 2, 2010, the entire disclosure of which is incorporated herein by reference.

BACKGROUND OF THE INVENTION

1. Field of the Invention

This invention relates to a virtual prosthetic limb system that can be used to design and evaluate new prosthetic limbs, serve as a platform for control algorithm design and sensor/signal selection, and train patients to use a given prosthetic limb.

2. Discussion of Related Art

Many individuals in the United States today are living with upper extremity amputations. These amputations most frequently result from trauma and affect young persons, especially for the soldiers wounded in Afghanistan or Iraq. A robotic arm with a fully functioning hand will significantly improve the quality of life for these amputees. Designing a robotic prosthetic arm with an optimal control mechanism that matches an individual's needs with minimum training time requires a lot of time, effort and money. A virtual prosthetic limb system that can simulate any possible design of prosthetic limb in a realistic way will significantly reduce the time, effort and money in developing a new robotic prosthetic limb, will reduce the actual training time for amputees to use the real prosthetic limbs and provide a platform for experimentation with any of a variety of possible control methods. Some research has been reported on creation of a virtual prosthetic arm system. In one such project, Orsborn, et al, (Orsborn, Amy et al, "Simulation of an Above-Elbow Myoelectric Prosthetic Arm for Development of an Implanted Myoelectric Control System", (http://www.phys.cwru.edu/undergrad/Senior%20Projects/SeniorProjectPosters/Amy-OrsbornPOSTER.pdf)), developed a basic prosthetic model and the framework required for a multi-component simulator using myoelectric signals. In another related project reported by J. Burck, M. J. Zeher, R. Armiger and J. D. Beaty, entitled "Developing the World's Most Advanced Prosthetic Arm Using Model-Based Design", and published by The Math Works in *News & Notes*, in 2009, they developed a Virtual Integration Environment (VIE) that included a limb simulation environment, constructed using MathWorks tools and Model-Based Design. The VIE allowed users to control the virtual prosthetic arm with different control inputs, e.g., switches or joysticks.

To develop a more advanced virtual prosthetic limb system, the present inventors adopted advanced technologies to, among other things (i) simulate the interactions between and among the virtual prosthetic limb and virtual objects; and (ii) to build a more realistic visualization system; and (iii) to "connect" the virtual prosthetic limb and the residual limb of a patient in two directions, namely, to change the position of the virtual prosthetic limb according to the movement of the residual arm of a patient, and to provide feedback to the patient according to the events in the virtual space. The inventive virtual prosthetic limb system can be used for designing and evaluating new prosthetic arms, as a platform for control algorithm design and sensor/signal selection, patient training, and recording limb movements and control signals during clinical investigations for performance analysis. For example, as a design platform it could be used in studying how to connect a robotic prosthetic arm into the nervous system and/or into the brain (see for example the publications "Extraction algorithms for cortical control of arm prosthetics" by Schwartz, A B, Taylor, D M, Tillery, S I, *Curr. Opin. Neurobiol.* 11, 701-707 (2001); "Cortical control of a prosthetic arm for self-feeding" by Velliste M, Perel S, Spalding M C, Whitford A S, Schwartz A B, *Nature*, Vol 453 19 Jun. 2008 doi:10.1038; and "Using virtual reality to test the feasibility of controlling an upper limb FES system directly from multiunit activity in the motor cortex" by Taylor D M, Schwartz A B, In Proceedings of the 6th Annual IFESS Conference: 2001 Jun. 16-20; Cleveland. 2001:132-134, all of which are incorporated by reference hereinto).

The inventors herein have recognized a need for a virtual prosthetic limb system that will minimize and/or eliminate one or more of the above-identified deficiencies.

SUMMARY OF THE INVENTION

The present invention provides a system for configuring a prosthetic limb for use by a living being.

A system in accordance with one embodiment of the invention includes an electronic control unit configured to receive a control signal generated in response to a command from the living being. The control unit is further configured to generate a plurality of virtual bodies on a display including, a plurality of members of a virtual prosthetic limb (e.g., fingers, a forearm, etc.) and at least one virtual object. The control unit is further configured to control movement of at least a first member of the plurality of members of the virtual prosthetic limb responsive to the control signal. The control unit is further configured to determine a contact force between first and second virtual bodies of the plurality of virtual bodies upon engagement between the first and second virtual bodies caused by movement of one of the at least a first member of the virtual prosthetic limb and the at least one virtual object. The first and second virtual bodies may comprise, for example, two members of the virtual prosthetic limb, two virtual objects, or a member of the virtual prosthetic limb and a virtual object. The control unit is further configured to adjust a position of at least one of the first and second virtual bodies responsive to the contact force.

A system in accordance with another embodiment of the invention includes an electronic control unit configured to receive a control signal generated in response to a command from the living being. The control signal may be generated through a control interface such as a switch or other conventional input/output device or through one or more sensors, such as an electrode placed in contact with tissue in the living being. The electronic control unit may be further configured to generate a virtual prosthetic limb and a virtual object on a display and to control movement of the virtual prosthetic limb responsive to the control signal (e.g., to sense movement of the residual limb and move the "attached" virtual prosthetic limb accordingly). The electronic control unit may be further configured to determine a contact force between the virtual prosthetic limb and the virtual object upon engagement of the virtual object by the virtual prosthetic limb. The electronic control unit may be further configured to adjust a position of at least one of the virtual prosthetic limb and the virtual object responsive to the contact force. In another embodiment of the invention, the electronic control unit may be further configured to generate a feedback signal to the living being responsive to engagement of the virtual object by the virtual prosthetic limb or another event in the virtual space.

A system in accordance with the present invention represents an improvement over conventional systems because it can efficiently simulate various designs for prosthetic limbs in a realistic manner. As a result, the system improves the design and evaluation of prosthetic limbs and associated control algorithms and sensor/signal selection and also provides more efficient training for patients.

These and other advantages of this invention will become apparent to one skilled in the art from the following detailed description and the accompanying drawings illustrating features of this invention by way of example.

DETAILED DESCRIPTION OF EMBODIMENTS OF THE INVENTION

Figure 1:
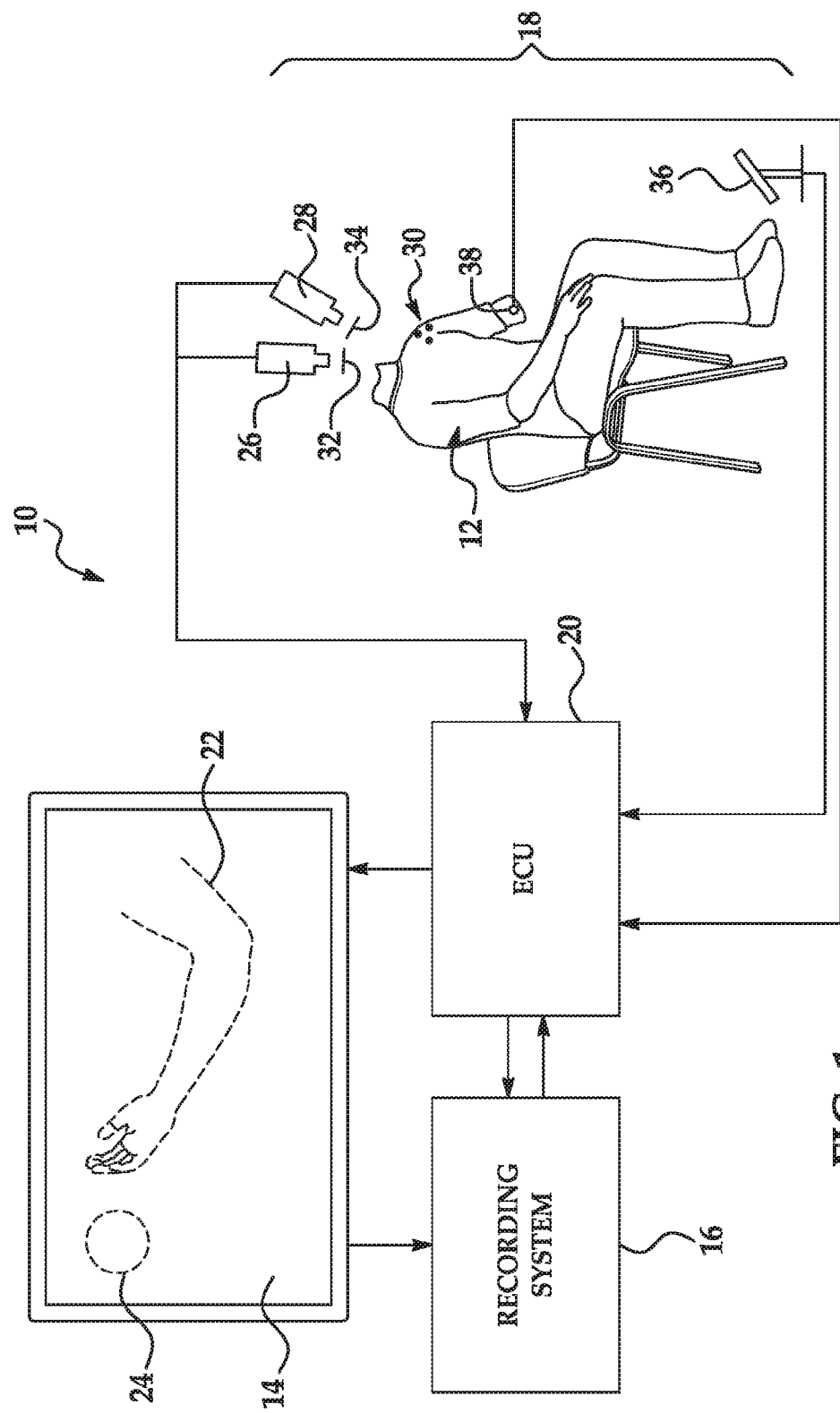
FIG. 1 is a diagrammatic view of one embodiment of a system in accordance with the present invention.

Referring now to the drawings wherein like reference numerals are used to identify identical components in the various views, FIG. 1 illustrates a system 10 for configuring a prosthetic limb for use by a patient 12 or other living being in accordance with one embodiment of the present invention. It should be understood that the term "limb" may refer to an arm, a leg, or any portion of the foregoing. System 10 may include a display 14, a recording system 16, a control interface 18, and an electronic control unit 20 in accordance with the present invention.

Display 14 is provided to display virtual bodies including a virtual prosthetic limb 22 and its constituent members (e.g., in the case of an arm, limb 22 may include an elbow joint, forearm, wrist joint, palm, fingers and finger joints) and one or more virtual objects 24 in order to allow patients 12 and others to visualize movement of the limb 22 in response to commands from the patient 12 and interactions with objects 24 and between objects 24 resulting from such movement. Display 14 may comprise a three-dimensional display. Display 14 may be a stereoscopic display or an auto-stereoscopic display. In one embodiment of the system stereoscopic 3D visualization of the virtual limb 22 and objects 24 is achieved by using the Alienware OptX™ AW2310 23-inch 3D Full HD Widescreen Monitor and NVIDIA GeForce 3D Vision Kit (both are available from Dell Computer, 1 Dell Way Round Rock, Tex.) with a 3D graphics card PNY NVIDIA Quadro FX 580 (available from Amazon.com). ECU 20 uses the application programming interface OpenGL originally developed by Silicon Graphics, Inc. to generate images of the limb 22 and objects 24 for left and right eyes and uses display 14 to achieve the stereoscopic 3D visualization. The virtual prosthetic limb 22 and virtual objects 24 will be rendered in real-time on display 14. The stereoscopic 3D display 14 will provide realistic visual sense and will improve the usage of system 10.

Recording system 16 is provided to record the positions of the virtual limb 22 and objects 24 as well as the set of commands from the subject/patient 12, at any given set of times. A set of images of the prosthetic limb 22 and virtual objects 24 can be regenerated using the recorded positions of the virtual limb 22 and virtual objects 24, for subsequent replaying on display 14 and/or computations or other outputs of ECU 20 for use in, for example, performance analysis. System 16 may comprise conventional fixed or portable media (e.g., a hard drive, compact disc, digital video disc, flash drive, etc.) and may be located locally or remotely and accessed over a wired or wireless telecommunications network. System 16 is configured to save and replay all movements of limb 22 and objects 24 for performance analysis.

Control interface 18 is provided to allow transfer of commands from the patient 12 to ECU 20 and, in some embodiments, to provide feedback from system 10 to patient 12. Interface 18 may generate control signals reflecting the patient's body movement so as to "attach" the patient's body to the virtual limb 22 by reflecting movement of the patient's body in the virtual space (e.g., a virtual arm with shoulder joint can be "attached" to the patient's shoulder and any movements (translations and/or rotations) of the patient's shoulder will move the virtual arm in real-time accordingly). Interface 18 may also generate control signals used to control movements of the joints that link the segments of the virtual limb (e.g., the elbow joint linking the upper arm and forearm, the wrist joint linking the forearm and hand, and knuckle joints linking finger segments).

In one embodiment of the invention, interface 18 includes a pair of cameras 26, 28, and a plurality of markers 30 that are affixed to the patient 12. The patient's body movements, e.g., shoulder movements, are measured in real-time with cameras 26, 28, mounted above the patient's shoulder. Cameras 26, 28, may be about 400 mm apart with camera 26 pointing vertically downward and camera 28 pointing downward at about thirty (30) degrees relative to camera 26. Three reflective tracking markers 30 forming a right triangle may be fixed on a 50 mm by 100 mm aluminum sheet (5 mm thick) coated with non-reflective paint. The sheet is mounted on the patient's shoulder in such a way that two of the markers 30 are in anterior-posterior direction (along the 50 mm side) and two markers 30 are in lateral-medial direction (along the 100 mm side). To avoid interference from extraneous light (e.g., room light), two infrared LED light sources (not shown) may be used to illuminate the tracking markers 30 and infrared filters 32, 34 may be used on the cameras 26, 28. The real-time tracking marker images captured by the two cameras 26, 28 are processed by ECU 20 to obtain the patient's shoulder translations and rotations. The processing by triangulation using video cameras and markers is well known in the field (see for example the publication "Repeatability of gait data using a functional hip joint centre and a mean helical knee axis," by Besier T. F., Sturnieks D. L., Alderson J. A. and Lloyd D. G., *J. Biomech.* 36 (2003), pp. 1159-1168, which is incorporated by reference hereinto). This information is used to determine the virtual prosthetic proximal end location and orientation. It should be understood that the above-described approach can also be used to capture the movements of other body parts, such as the residual limb of an above-elbow amputee. In an alternative embodiment, control interface 18 may include a position sensor (not shown) affixed to the patient 12 and a tracking device such as the electromagnetic motion analysis system sold commercially under the trademark "FASTRAK" by Polhemus Inc. of Colchester, Vt. The sensors may be placed on the trunk and residual limb and 3D position coordinates and angles (roll, pitch, and yawl) are measured and transmitted to ECU 20. The sensor and tracking device may be connected by wires or cables or may exchange data wirelessly through, for example, radiofrequency or infrared transmitters and receivers or the like.

As noted hereinabove, control interface 18 may also include means for receiving signals used to control joints in limb 22. In one embodiment of the invention, interface 28 may include switches 36 operated by the patient's feet used to control the movements of the joints and various segments connected by those joints in the virtual limb 22. The patient 12 can use the switches 36 to move an individual segment, e.g., rotate the forearm to pour water into a cup, or to move segments in a group, e.g., move hand to a given point in a 3D space, or control fingers to grab or release an object. In an alternative embodiment, interface 18 includes one or more sensors, such as an accelerometer, attached to patient 12. In yet another alternative embodiment, one or more electrodes 38 may be attached to tissue (e.g., muscle or nerve tissue) in the residual limb of the patient. Electrodes 38 are used to obtain myoelectric signals from a patient and the signals are used to control the movements of the segments of limb 22. It should be appreciated that a variety of control signals besides those arising from switches 36 or electromyography (EMG) signals detected by sensors 38 can be used in the present invention. For example, EEG and direct electrode recording from within the brain, or any combination of the above, are all considered to be within the scope of the present invention.

ECU 20 provides a means for generating virtual bodies on display 14 including members of limb 22 and objects 24 and for controlling movement of limb 22 and its members. ECU 20 further provides a means for determining a contact force between various virtual bodies (e.g. between members of limb 22, between limb 22 and an object 24 or between two objects 24) upon engagement between the virtual bodies resulting from movement of one or more members of limb 22 or one or more virtual objects 24. ECU 20 further provides a means for adjusting a position of at least one of the virtual bodies responsive to the contact force. ECU 20 may comprise a programmable microprocessor or microcontroller or may comprise an application specific integrated circuit (ASIC). ECU 20 may include a central processing unit (CPU) and an input/output (I/O) interface through which ECU 20 may receive a plurality of input signals including signals generated by control interface 18 and generate a plurality of output signals including those used to control and/or provide data to display 14 and recording system 16.

In accordance with one embodiment of the present invention, ECU 20 is configured with appropriate programming instructions or code (i.e., software) to perform several steps in a method for configuring a prosthetic limb 22 in accordance with the present invention. The method may include the step of receiving one or more control signals generated in response to a command from the patient 12. These control signals may be generated by control interface 18 as described hereinabove. The method may continue with the steps of generating a virtual prosthetic limb 22 (and individual members of limb 22) and one or more virtual objects 24 on display 14 and controlling movement of members of limb 22 responsive to the control signals. ECU 20 may generate limb 22 and objects 24 using the application programming interface OpenGL originally developed by Silicon Graphics, Inc. ECU 20 calculates the translations and rotations of each segment of limb 22 based on the control signals from interface 18 and the movements of objects 24 according to the interaction between limb 22 and objects 24 or between multiple objects 24. The movement of limb 22 is therefore controlled by the real-time input signals from interface 18. The patient's body movements will be directly reflected in the virtual prosthetic limb 22. The joint movements will be controlled in the way as designed, e.g., each individual joint or group of joints will be controlled to realize pre-defined movements.

Figure 2A:
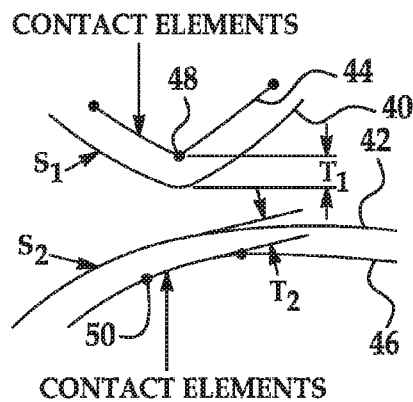
FIGS. 2A-B are diagrammatic views of surfaces of two virtual objects (e.g., a virtual prosthetic limb and another virtual object) before and after contact between the two surfaces.
Figure 2B:
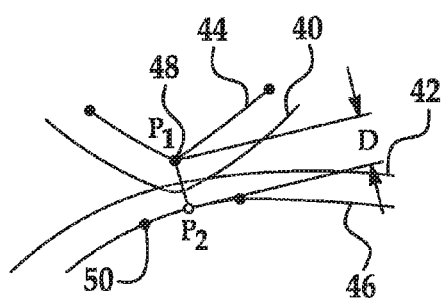
Figure 3A:
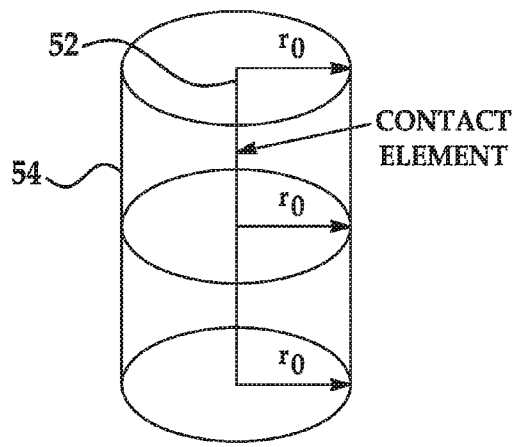
FIGS. 3A-B are diagrammatic views of exemplary contact elements within a virtual object.
Figure 3B:
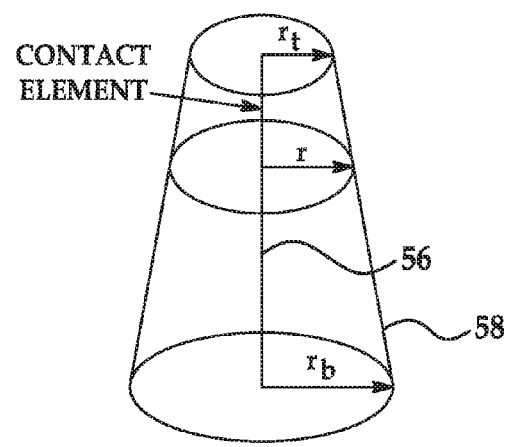

Referring to FIG. 2, limb 22 and objects 24 are defined to include one or more surfaces 40, 42 and a plurality of contact elements 44, 46 having a predetermined relationship (e.g. location) to a given surface 40, 42. Each contact element 44, 46 further includes one or more contact nodes 48, 50. Contact elements 44, 46 with contact nodes 48, 50 will be used to cover all surfaces 40, 42 that may contact with other surfaces 40, 42 for both virtual limb 22 and virtual objects 24. In one embodiment of the invention, three (3) node triangle contact elements are used to represent the surfaces in three-dimensional space. It should be appreciated, however, that different approaches with respect to the specific choice of contact elements 44, 46 can be adopted. For example, in two alternative embodiments, four and eight node quadrilateral contact elements, respectively, are used. It should be appreciated that a variety of shapes and number of nodes 48, 50 for the contact elements 44, 46 should be considered to be within the scope of the present invention. Referring to FIGS. 3A-B, two alternative embodiments of contact elements are shown that may reduce computational overhead. In FIG. 3A, a linear or line contact element 52 is placed in the center of a virtual cylindrical object 54 (which may comprise a portion of a virtual limb 22 for example) In FIG. 3B, a linear or line contact element 56 is placed in the center of a virtual cylindrical-conical object 58 (which may comprise a portion of a virtual limb 22 such as a finger or section of a finger for example). In another alternative embodiment, a single node contact element with a shape of a point is placed in the center of a virtual spherical object and with contact tolerance equal to the radius of the spherical object. This embodiment is useful for significantly reducing cost (in terms of processing time and memory) in processing the interactions between the spherical object and virtual limb 22 or other virtual objects 24. The contact elements 44, 46 may have complete or continuous coverage over a given surface or only a portion thereof. Alternatively, the contact elements 44, 46 may not have complete or continuous coverage over a given surface or portion thereof. In such embodiments, contact elements composed of circles, triangles or other shapes (e.g. a point) are relatively sparsely distributed over contact surfaces.

Each contact element 44, 46 may be placed beneath a given surface 40, 42 with an offset (i.e., depth) equal to the contact tolerance of the element 44, 46. In one embodiment, it is assumed that the contact elements 44, 46 do not move relative to the original contact surfaces 40, 42 when the contact surfaces 40, 42 deform. It should be appreciated that in the scope of the present invention a variety of tolerances may be used, including a variety of tolerances below a given surface, above a given surface and on a given surface and that, in some embodiments the contact elements 44, 46 can move relative to the original contact surfaces 40, 42 when the contact surfaces deform. In the embodiment of the contact element 52 shown in FIG. 3A, the contact tolerance is equal to the fixed radius $r_0$. In FIG. 3B, the tolerance varies along the length of element 56 and is equal to the varying radius r at that point. In the illustrated embodiment, $r_t$ and $r_b$ are the radii at the top and bottom of the virtual object 58, respectively.

The inventive method may further include the step of determining a contact force between a pair of virtual bodies upon engagement between the virtual bodies caused by movement of limb 22 or one or more virtual objects 24. In one embodiment of the invention, the contact force between virtual prosthetic limb 22 (or at least a member thereof) and a virtual object 24 is determined. Alternatively, it should be understood that the contact force between multiple members of limb 22 could be determined (e.g., one finger engaging another finger) or between multiple virtual objects could be determined (e.g., a baseball bat swung by the virtual limb hitting a ball). Each contact element 44, 46 has its own contact properties, including contact tolerance, stiffness, maximum allowed force, minimum separation force and coefficient of friction. In one embodiment of the invention, it is assumed that contact properties do not vary within a contact element 44, 46. In an alternative embodiment of the invention, contact properties may vary within an element 44, 46. The concept of the contact tolerance is introduced by the inventors to effectively process interactions between the virtual bodies such as limb 22 and virtual objects 24. In general, the contact tolerance of a contact element 44, 46 is the distance beneath the surface 40, 42 (or relative to the surface 40, 42) at which the contact element 44, 46 is located. With this approach, contact force and displacement of a contact node 48, 50 or contact point can be easily calculated (see description below). For contact stiffness, an elastic force-displacement relationship is used. In some embodiments, a linear elastic relationship F=k×d, where K is a constant, is used although non-linear relationships may find application in several embodiments in which surfaces have large deformations. In an alternative embodiment of the invention where contact properties vary within an element 44, 46, stiffness has a more complicated force-displacement relationship, e.g., different loading-unloading-reloading curves, including creep and stress relaxation, so that more complicated interactions between the virtual limb 22 and virtual objects 24 can be simulated (such as squeezing toothpaste).

Referring again to FIGS. 2A-B, two surfaces $S_1$ and $S_2$ are shown with contact points $P_1$ and $P_2$ before contact is established (FIG. 2A) and after contact is established (FIG. 2B). In the illustrated embodiment, contact point $P_1$ comprises contact node 48. It should be understood, however, that either of contact points $P_1$ and $P_2$ may comprise a contact node or another point on surface $S_1$ and $S_2$, respectively. $T_1$ and $T_2$ are the contact tolerances of contact points $P_1$ and $P_2$, respectively. D is the distance between $P_1$ and $P_2$. In the illustrated embodiment, contact elements 44, 46 are disposed beneath the surfaces 40, 42 at predetermined offsets (i.e., the depths below the surfaces) equal to the contact tolerances for the points $P_1$, $P_2$, respectively. ECU 20 may be configured, in determining the contact force, to detect a condition in which a distance between a point $P_1$ on a first contact element 44 of limb 22 and a point $P_2$ on a contact element 46 of object 24 is less than a sum of a tolerance of point $P_1$ and of a tolerance of point $P_2$ and, upon detecting the condition, calculate the contact force responsive to one of the predetermined set of characteristics associated with the contact nodes 48, 50 of the contact elements 44, 46 of limb 22 and object 24. In particular, when the distance D between a contact point $P_1$ on a surface $S_1$ and a contact point $P_2$ on another surface $S_2$ becomes less than the summation of the contact tolerances $T_1$, $T_2$ associated with the two contact points $P_1$, $P_2$, contact force may be calculated based on the stiffnesses of the contact points $P_1$, $P_2$. When two surfaces (e.g. surfaces 40, 42) contact each other, two cases are considered: (1) a contact point $P_1$, $P_2$ from one of the two surfaces 40, 42 contacts a contact point $P_1$, $P_2$ on the other surface 40, 42 that is within the perimeter of a contact element 44, 46; and (2) a contact point $P_1$, $P_2$ on one surface 40, 42 contacts a point $P_1$, $P_2$ on the other surface 40, 42 where one or more contact elements 46, 48 touch. The contact properties of a contact point $P_1$, $P_2$ for these two cases are defined as (1) the same as the contact element 44, 46, when the contact point $P_1$, $P_2$ is within the perimeter of the contact element 44, 46; and (2) the same as the contact element 44, 46 or the angular weighted average of all contact elements 44, 46 that touch the point $P_1$, $P_2$. ECU 20 may be further configured, in determining the contact force, to determine a direction of the contact force responsive to a position of the points $P_1$, $P_2$ on the contact elements 44, 46. In particular, the direction of the contact force may be defined as the line segment between the two contact points $P_1$, $P_2$. Friction force associated with the contact force may also be calculated. The contact force, F, is a known function of displacement, and this function is referred to as "stiffness", denoted by F(d). The contact force is calculated in the following way: the contact force applied on the contact points $P_1$ and $P_2$ is $$F=F_1(d_1)=F_2(d_2)$$

where $d_1$ is the displacement of the contact point $P_1$ and $F_1(d_1)$ is a known function of $d_1$, representing the contact force on contact point $P_1$ due to the displacement $d_1$, and the $d_2$ and $F_2(d_2)$ are the displacement and force associated with contact point $P_2$. The phrase "displacement of a contact point" stands for the normal (i.e., orthogonal) deformation of a contact surface in an area represented by the contact point. The contact forces on each of the two surfaces (which are equal in magnitude and opposite in direction) can be computed as follows. Referring to FIG. 2, by equating $d_1+d_2$ to the difference between the summation, $T_1+T_2$, of the contact tolerances of the two contact points $P_1$, $P_2$, respectively, and the distance, D, between the two contact points $P_1$, $P_2$, the contact force is obtained by solving the two equations $$F_1(d_1)=F_2(d_2) \text{ and } T_1+T_2-D=d_1+d_2$$

In most embodiments of the invention, the contact force and displacement of each contact point $P_1$, $P_2$ are calculated independently of any other contact point $P_1$, $P_2$. In an alternative embodiment of the invention, the contact force and displacement of a contact point $P_1$, $P_2$ depend on the contact force and displacement of one or more other contact points $P_1$, $P_2$. In yet further alternative embodiments, computational modeling, e.g., the finite element method, boundary element method and/or finite difference method, are used to calculate the contact forces and deformations of the segments of the virtual limb 22 and the virtual objects 24, due to the surface forces (e.g., contact and friction forces) and body forces (e.g., gravity and electromagnetic forces) in the virtual space. Such computational methods are well known in the art; see for example the excellent three books:

1. "The finite element method for solid and structural mechanics", By O. C. Zienkiewicz, Richard Lawrence Taylor, Robert Leroy Taylor Sixth edition published by Butterworth-Heinemann 2005;
2. "Boundary Element Techniques in Engineering", By C. A. Brebbia, First edition published by Newnes-Butterworths 1980; and
3. "The finite difference method in partial differential equations", MITCHELL, A R, GRIFFITHS, D F, Chichester, Sussex, England and New York, Wiley-Interscience, 1980, all of which are incorporated by reference hereinto.

The inventive method may continue with the step of adjusting a position of at least one of the virtual bodies such as prosthetic limb 22 or virtual object 24 responsive to the determined contact force. The movements of a virtual movable object 24 will be determined by the resultant of all forces (and moment of forces) applied on the object 24 and the mass (and moment of inertia) of the object 24, as well as the environment simulated, e.g., on the earth, in a weightless space, under water or a hypothetical environment. If a contacting virtual object 24 is fixed in space, e.g., a virtual workbench, the movements of the virtual limb 22 or a movable object 24 will be limited when they contact such a virtual object 24. A virtual object 24 with limited movements may become a movable object when the resultant of forces applied on the object 24 is higher than a threshold level, e.g., picking an apple from a tree. ECU 20 may be further configured, in adjusting the position of a virtual body such as the virtual prosthetic limb 22 and/or virtual object 24, to limit an amount of an adjustment from a prior position to an amount that is less than a predetermined minimum distance between the contact points $P_1$, $P_2$ on the virtual bodies. To prevent penetration between two contact elements 44, 46, the movements of the virtual limb 22 and virtual objects 24 will be achieved by adopting multiple small incremental movements, so that the maximum displacement of all (any) contact elements 44, 46 will be smaller than the minimum contact tolerance of all contact elements 44, 46 before any contact is established. The increments may be reduced further to ensure the maximum displacement will be smaller than the minimum distance between any pair of contact points $P_1$, $P_2$ after any contact is established. Surface contact may be checked from both sides of two contact surfaces, i.e., to ensure that contact points $P_1$, $P_2$ on one contact surface 40, 42 do not penetrate any contact element 44, 46 on another contact surface 40, 42 and vice versa. In yet further embodiments, surface contact is checked asymmetrically; that is, it is only ensured that contact points $P_1$, $P_2$ on one contact surface 40, 42 do not penetrate any contact element 44, 46 on another contact surface 40, 42, but the reverse is not checked. For example, this would be equivalent to ensuring that the contact point $P_1$ on the virtual limb 22 does not penetrate any contact element 46 on the contact surfaces 42 of the virtual objects 24, but that the contact surfaces 42 of the virtual objects 24 are not checked to ensure no penetration onto the virtual limb 22. In one embodiment of the invention, deformations of the virtual limb 22 and virtual objects 24 due to contact forces are not reflected by ECU 20 on display 14. In an alternative embodiment of the invention, the deformations are reflected on display 14.

ECU 20 may be further configured to generate virtual force sensors at various locations on virtual prosthetic limb 22 (e.g., on the fingers) and to transmit an output signal through an interface to the patient 12 or others responsive to a contact force determined at the location of a given virtual force sensor. The interface may be a part of, or separate from, interface 18. Further, although ECU 20 is used to process signals from the virtual sensors and/or provide output signals to the interface, it should be understood that the interface could employ a separate electronic control unit to process the signals and provide output signals to the interface such that signal processing for the interface can be designed independent of the other tasks handled by ECU 20. Forces sensed at the virtual sensor locations may be fed back to the patient 12 or others with visual and/or audio output signals. For example, the contact forces calculated by ECU 20 at the location with virtual force sensors may be displayed on display 14 or a separate display. ECU 20 may also generate sounds through an audio interface that mimics expected sounds from the interaction of limb 22 and objects 24 (e.g., a hand hitting a table, objects contacting one another, or a can being crushed by a hand). Forces sensed at the virtual sensor, locations may also be fed back to patient 12 through electro-mechanical feedback mechanisms. For example, ECU 20 may generate a signal through an electrode coupled to the patient's residual limb, to simulate the interaction in virtual space (e.g., contact of the limb and other objects, inertia force due to limb and object motions, etc.). The output signal may have a predetermined characteristic if the contact force exceeds a predetermined threshold. For example, when the maximum force at a given location becomes higher than a preset level, a visual and/or audio warning signal may be provided.

In yet another alternative embodiment, the virtual limb 22 or limbs are used to simulate a person's natural limb or limbs instead of a prosthetic limb. In this embodiment, tracking markers are placed on segments of the natural limb(s) to capture the real-time movements of the interested segments and the captured real-time data is used to control the movements of the virtual limb(s).

While the invention has been shown and described with reference to one or more particular embodiments thereof, it will be understood by those of skill in the art that various changes and modifications can be made without departing from the spirit and scope of the invention.

We claim:

1. A system for configuring a prosthetic limb for use by a living being, comprising:
   an electronic control unit configured to
      receive a control signal generated in response to a command from said living being
      generate a plurality of virtual bodies on a display including a plurality of members of a virtual prosthetic limb and at least one virtual object;
      control movement of at least a first member of said plurality of members of said virtual prosthetic limb responsive to said control signal;
      determine a contact force between first and second virtual bodies of said plurality of virtual bodies upon engagement between said first and second virtual bodies caused by movement of one of said at least a first member of said virtual prosthetic limb and said at least one virtual object; and,
      adjust a position of at least one of said first and second virtual bodies responsive to said contact force.

2. The system of claim 1 wherein said first virtual body comprises said first member of said virtual prosthetic limb and said second virtual body comprises a second member of said virtual prosthetic limb.

3. The system of claim 1 wherein said first virtual body comprises said first member of said virtual prosthetic limb and said second virtual body comprises a first virtual object.

4. The system of claim 1 wherein said first virtual body comprises a second member of said virtual prosthetic limb and said second virtual body comprises a first virtual object.

5. The system of claim 1 wherein said first virtual body comprises a first virtual object and said second virtual body comprises a second virtual object.

6. A system for configuring a prosthetic limb for use by a living being, comprising:
   an electronic control unit configured to
      receive a control signal generated in response to a command from said living being
      generate a virtual prosthetic limb and a virtual object on a display;
      control movement of said virtual prosthetic limb responsive to said control signal;
      determine a contact force between said virtual prosthetic limb and said virtual object upon engagement of said virtual object by said virtual prosthetic limb; and,
      adjust a position of at least one of said virtual prosthetic limb and said virtual object responsive to said contact force.

7. The system of claim 6, further comprising a control interface configured to generate said control signal.

8. The system of claim 7, wherein said control interface comprises a foot activated switch.

9. The system of claim 7 wherein said control interface includes:
   a plurality of markers configured to be affixed to said living being; and,
   first and second cameras generating images of said markers.

10. The system of claim 7 wherein said control interface includes a sensor.

11. The system of claim 10 wherein said sensor comprises an accelerometer configured for attachment to said living being.

12. The system of claim 10 wherein said sensor comprises an electrode configured to contact tissue in said living being.

13. The system of claim 6 wherein said display comprises a three dimensional display.

14. The system of claim 6 wherein said virtual prosthetic limb includes a first surface and a first plurality of contact elements located at a predetermined position relative to said first surface, each of said first plurality of contact elements having at least one contact node having a predetermined set of characteristics and said virtual object includes a second surface and a second plurality of contact elements located at a predetermined position relative to said second surface, each of said second plurality of contact elements having at least one contact node having a predetermined set of characteristics.

15. The system of claim 14 wherein said electronic control unit is further configured, in determining said contact force, to:
detect a condition in which a distance between a contact point on a first contact element of said virtual prosthetic limb and a contact point on a first contact element of said virtual object is less than a sum of a tolerance of said contact point on said first contact element of said virtual prosthetic limb and of a tolerance of said contact point on said first contact element of said virtual object; and,
upon detecting said condition, calculate said contact force responsive to one of said predetermined set of characteristics of said at least one contact node of said first contact element of said virtual prosthetic limb and said predetermined set of characteristics of said at least one contact node of said first contact element of said virtual object.

16. The system of claim 15 wherein said electronic control unit is further configured, in determining said contact force, to determine a direction of said contact force responsive to a position of said contact point on said first contact element of said virtual prosthetic limb and a position of said contact point on said first contact element of said virtual object.

17. The system of claim 14 wherein said predetermined set of characteristics includes at least one characteristic selected from the group consisting of: contact tolerance, stiffness, maximum allowed force, minimum separation force and coefficient of friction.

18. The system of claim 14 wherein said electronic control unit is further configured, in adjusting said position of at least one of said virtual prosthetic limb and said virtual object, to limit an amount of an adjustment from a prior position to an amount that is less than a predetermined minimum distance between a contact point on a first contact element of said virtual prosthetic limb and a contact point on a first contact element of said virtual object.

19. The system of claim 6 wherein said electronic control unit is further configured to transmit an output signal through an interface to said living being responsive to said contact force.

20. The system of claim 19 wherein said output signal has a predetermined characteristic if said contact force exceeds a predetermined threshold.

* * * * *